United States Patent
D'Alise

(10) Patent No.: US 9,974,631 B2
(45) Date of Patent: *May 22, 2018

(54) SINUS LIFT PROCEDURE AND SIDECUTTING DRILL

(71) Applicant: David D'Alise, Albuquerque, NM (US)

(72) Inventor: David D'Alise, Albuquerque, NM (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/729,116

(22) Filed: Oct. 10, 2017

(65) Prior Publication Data

US 2018/0028291 A1    Feb. 1, 2018

Related U.S. Application Data

(62) Division of application No. 14/073,859, filed on Nov. 6, 2013.

(60) Provisional application No. 61/723,201, filed on Nov. 6, 2012.

(51) Int. Cl.
*A61C 5/00* (2017.01)
*A61C 8/00* (2006.01)
*A61C 3/02* (2006.01)

(52) U.S. Cl.
CPC .............. *A61C 8/0092* (2013.01); *A61C 3/02* (2013.01); *A61C 8/0089* (2013.01)

(58) Field of Classification Search
CPC ...... A61C 8/0092; A61C 3/02; A61B 17/1785
See application file for complete search history.

*Primary Examiner* — Heidi M Eide
(74) *Attorney, Agent, or Firm* — Snell & Wilmer L.L.P.

(57) ABSTRACT

A method of performing a sinus lift procedure comprising the use of a sidecutting drill as one step in the procedure. The sidecutting drill creates a circumferential lateral cut near the sinus floor, thereby allowing upfracturing of the sinus floor over a greater area than would otherwise be possible absent the circumferential lateral cut. The sidecutting drill includes a tip extending in a planar nonuniform manner from the centerline of said drill with one or more cutting edges located on the extended portion for cutting through tissue.

5 Claims, 11 Drawing Sheets

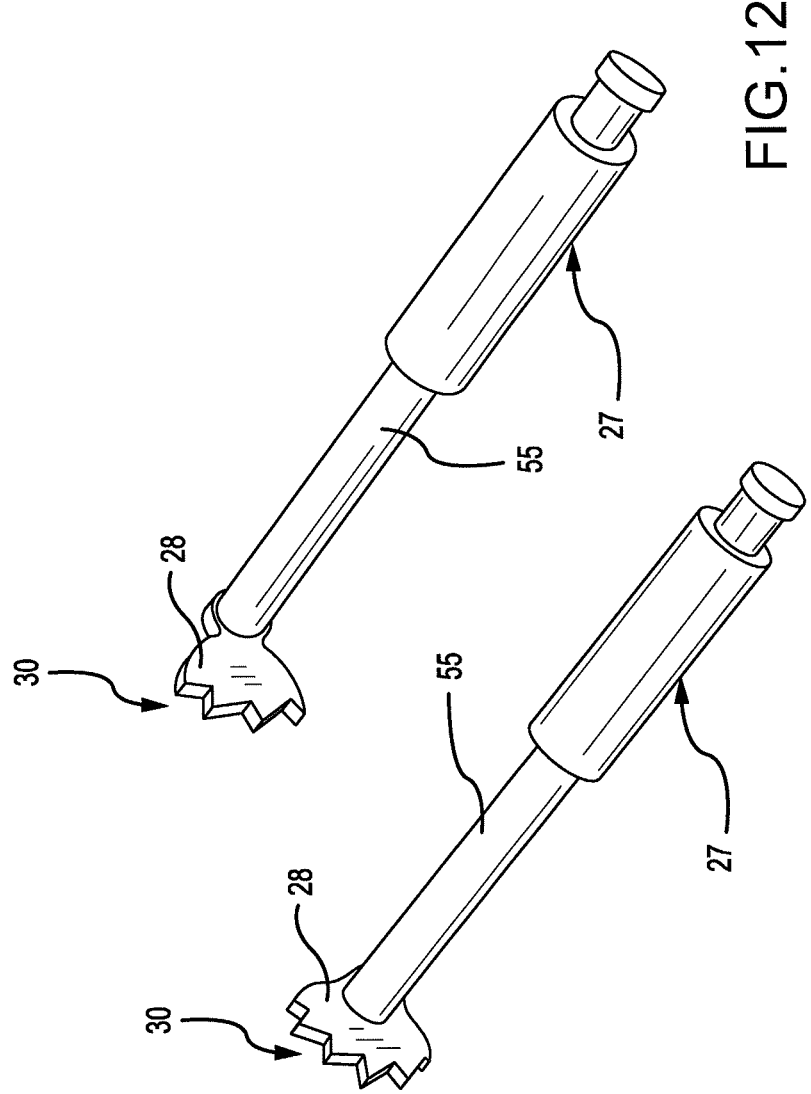

SINUS LIFT PROCEDURE AND SIDECUTTING DRILL

Figure 1:
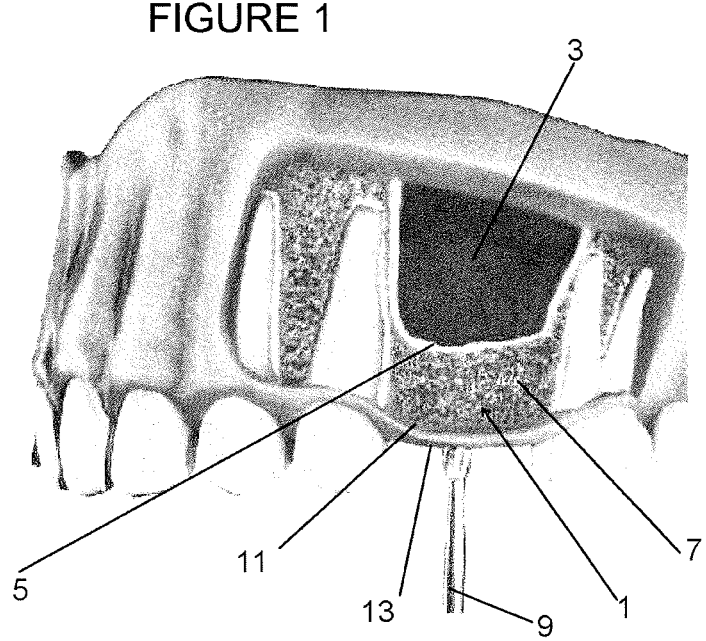

This application claims priority to and the benefit of U.S. Provisional Patent Application Ser. No. 61/723,201, entitled "Socket/Sinus Lift Procedure and Sidecutting Drill Bit," filed on Nov. 6, 2012, and U.S. patent application Ser. No. 14/073,859, entitled "Sinus Lift Procedure and Sidecutting Drill", filed on Nov. 6, 2013, the entirety of which are incorporated herein by reference as part of the disclosure of this application.

The present invention relates generally to the field of dental surgery, and more particularly to the placement of dental implants in a patient's mouth and equipment used in such a procedure. More particularly, the invention comprises a procedure for performing a socket/sinus lift or trans alveolar procedure as part of the placement of a dental implant in a patient's upper jawbone. The invention also includes a sidecutting or lateral relief drill bit that is used as part of the procedure, with the provision of a kit containing instrumentation/tools needed to perform a sinus lift procedure, including the sidecutting drill.

BACKGROUND

In cases where insufficient bone or non-ideal bone conditions are presented, bone grafting can be used to increase the volume and/or density of the bone at the desired dental implant placement site. With respect to the present invention, bone grafting is a procedure whereby bone is rebuilt in areas of the upper jaw that are bone-deficient in the areas under the sinuses. Lifting the sinus floor and or membrane and bone grafting allows the placement of ideally sized dental implants of sufficient length in situations where there is otherwise insufficient or nonideal bone condition. A sinus lift or socket/sinus or trans alveolar lift technique is used. The maxillary sinus is a hollow area in the upper jawbone above the teeth posterior to the canines. Bone volume at or near the sinus may be insufficient for implant placement for a number of reasons, including but not limited to bone loss due to disease or just plain disuse atrophy over time after having the teeth removed. In such situations, attempting to place an implant may push it up into the maxillary sinus due to the noted lack of bone or just plain not having sufficient bone to place a root form implant. Using a sinus/socket or trans alveolar lift technique in such situations provides the sufficient bone height necessary for placement of an implant, and the technique involves lifting the sinus membrane to allow bone grafting (sometimes the technique is generically referred to as a sinus augmentation).

The socket/sinus or trans alveolar lift technique involves an approach from the extraction cavity or healed alveolar crest with an osteotomy to just below the floor of the maxillary sinus, and the cavity space is gradually filled with grafted bone (or an artificial/synthetic bone grafting material) to push up the Schneiderian membrane (the lining of the maxillary sinus cavity) to obtain sufficient bone thickness for implant placement.

SUMMARY OF THE INVENTION

In the present invention, the sidecutting drill bit used in the flat topped socket or osteotomy formed previously with a series of drills designed to achieve it, makes a thin cut perpendicular to the socket or osteotomy extending laterally just under the sinus floor. The head or tip shape as shown in the figures, and the drill may be any of a number of sizes required by the diameter of the implant to be used in the procedure. When inserted into the osteotomy, the sidecutting bit allows a circumferential sidecutting or relief cutting action. Such action allows the floor of the sinus to be lifted as described in the detailed description below of the procedure with up-fracturing of the sinus floor over a greater/wider area than would be possible absent the sidecutting. The procedure thus also allows a greater amount or depth of bone grafting material to be placed in the osteotomy site but more importantly allows for more alveolar bleeding into the site than would be possible absent the sidecutting. The procedure itself enables the placement of an implant into a bone site otherwise lacking sufficient bone to allow the desired length of dental implant placement. The procedure comprises creating an osteotomy in the existing bone toward the sinus floor, generating a lateral relief cut with the previously mentioned lateral relief drill bit, and pushing bone grafting material into the hole and lifting the sinus floor by up fracturing the floor lateral to the osteotomy circumferentially enabling alveolar bone bleeding into the bone grafting material inserted. That is followed by appropriate placement of an appropriate implant through the bone into the grafted area reducing the time for resolution of the graft transforming it into natural bone around the implant and allowing it (the implant) to be placed in function in a fraction of the usual time.

BRIEF DESCRIPTIONS OF DRAWINGS

FIG. 1: Perspective view of an edentulous area (cutaway to show sinus cavity) depicting use of surgical bur.

Figure 2:
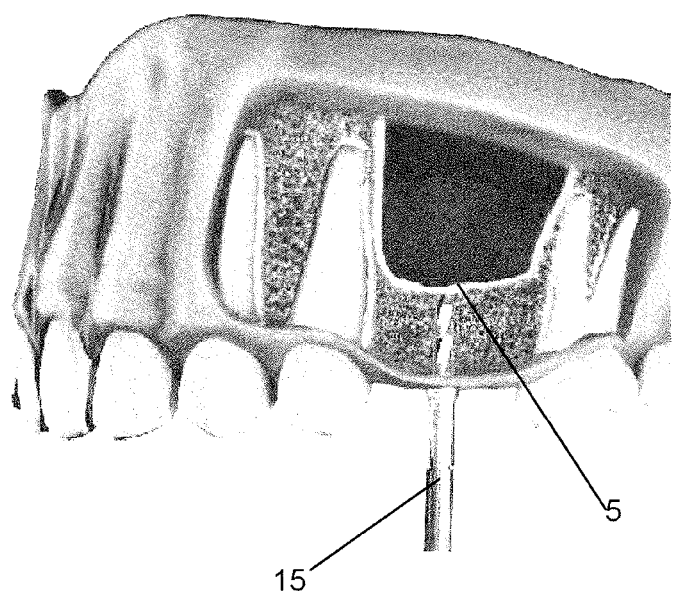

FIG. 2: Perspective view of an edentulous area (cutaway to show sinus cavity) depicting use of pilot drill.

Figure 3:
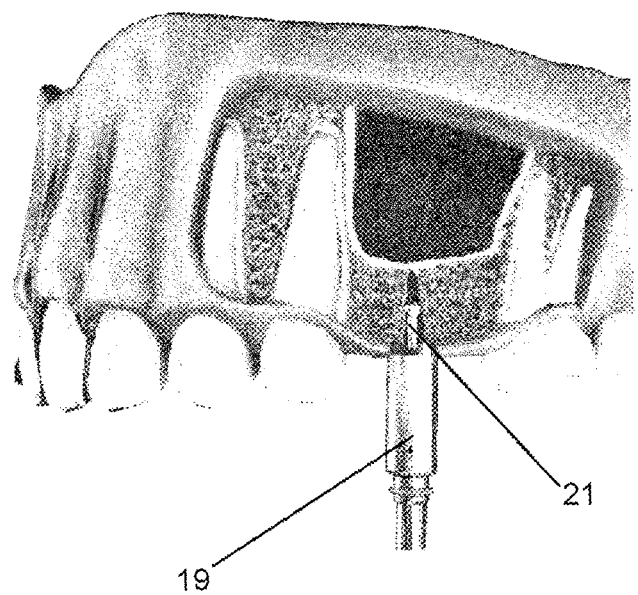

FIG. 3: Perspective view of an edentulous area (cutaway to show sinus cavity) depicting use of tissue punch with center guide pin.

Figure 4:
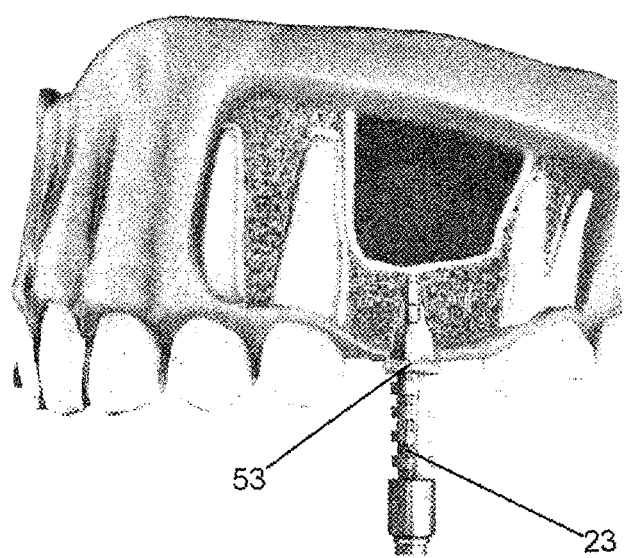

FIG. 4: Perspective view of an edentulous area (cutaway to show sinus cavity) depicting use of osteotomy former/enlarger drill to allow the entrance of the larger diameter flat topped osteotomy former.

Figure 5:
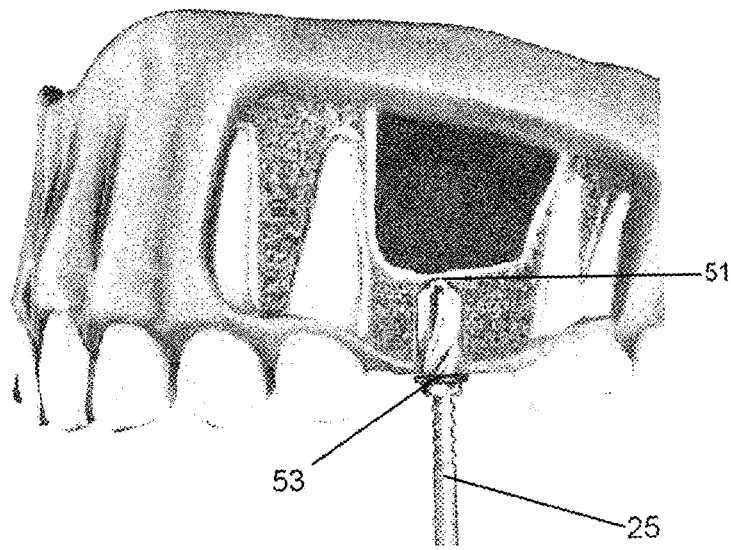

FIG. 5: Perspective view of an edentulous area (cutaway to show sinus cavity) depicting use of flat top with extended dimple (half-sphere shaped protrusion) to 1 to 2 mm short of the sinus floor drill.

Figure 6:
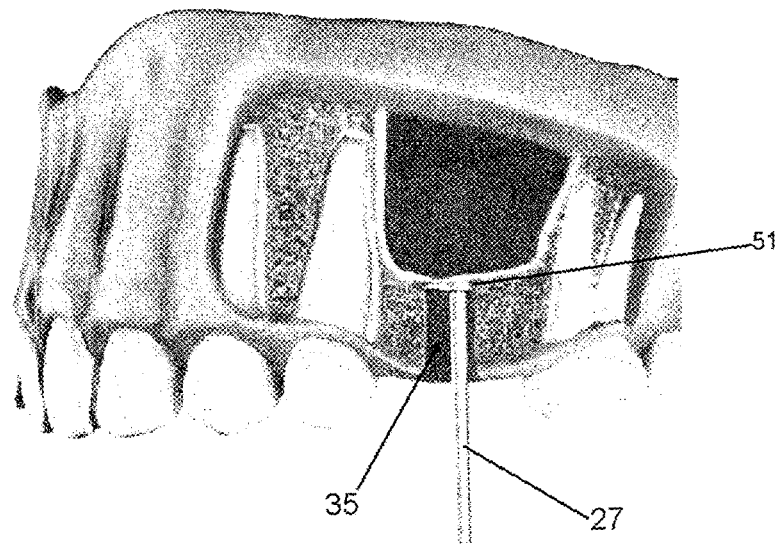

FIG. 6: Perspective view of an edentulous area (cutaway to show sinus cavity) depicting use of sidecutting (lateral relief) drill, wherein the shank or shaft is moved circumferentially around the osteotomy hugging the wall creating the 360 degree relief cut at the top when viewing the figure (actually the bottom of the osteotomy).

Figure 7:
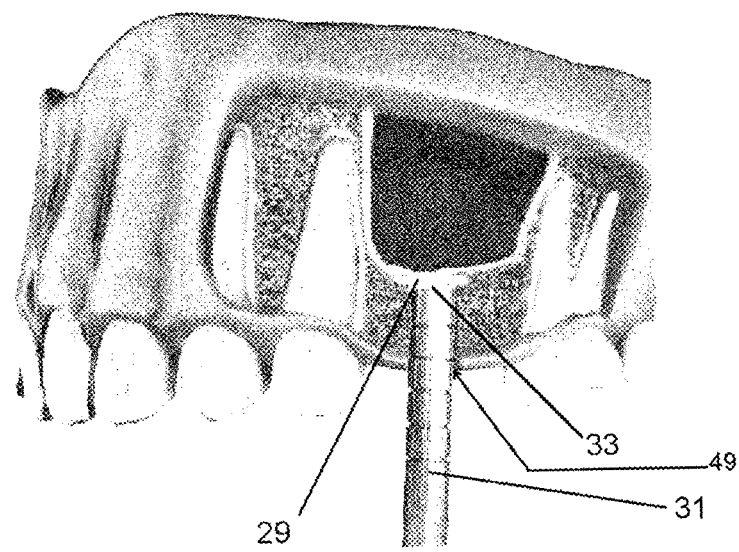

FIG. 7: Perspective view of an edentulous area (cutaway to show sinus cavity) depicting use of absorbable collagen wound dressing to protect the fragile membrane from tearing or puncture.

Figure 8:
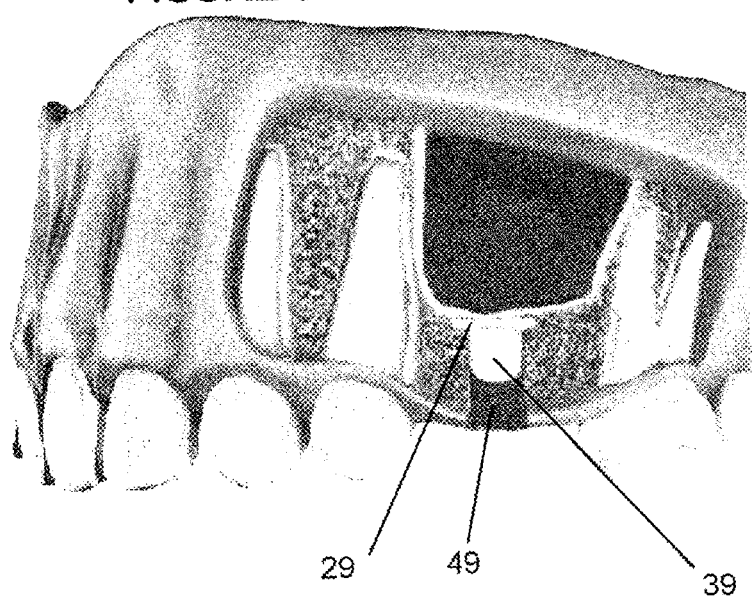

FIG. 8: Perspective view of an edentulous area (cutaway to show sinus cavity) depicting filling osteotomy grafting material of choice.

Figure 9:
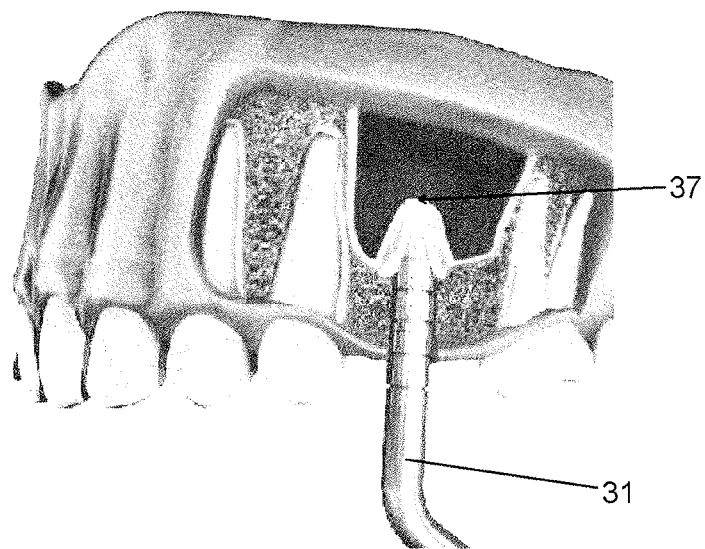

FIG. 9: Perspective view of an edentulous area (cutaway to show sinus cavity) depicting use of concave tip osteotome to lift floor of the sinus by pushing on the cushioning graft material thus up fracturing the thin cortical boney sinus floor at the limits of the lateral cut exposing the graft to bleeding from the underlying alveolar bone.

Figure 10:
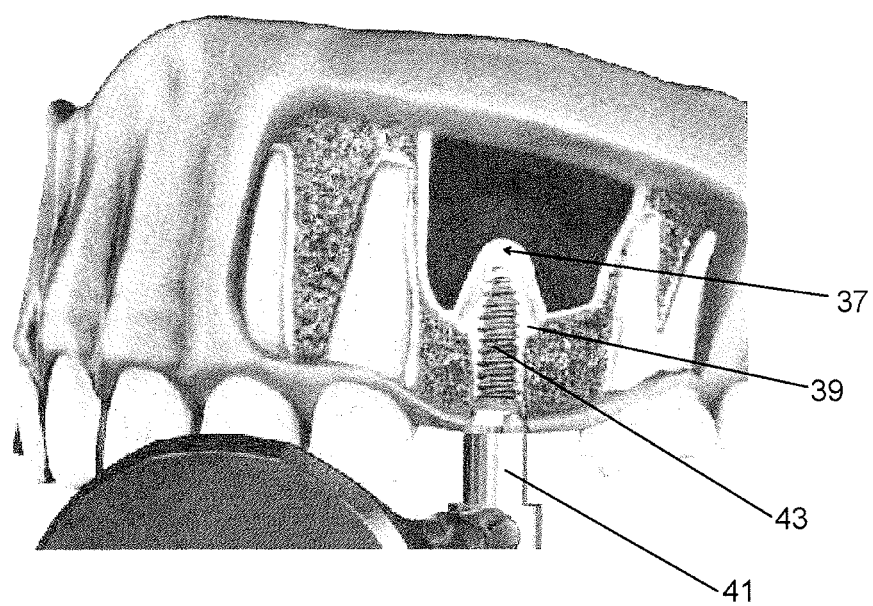

FIG. 10: Perspective view of a previously-edentulous area (cutaway to show sinus cavity) depicting placement of implant and the up fracturing of the sinus floor exposing the alveolar below and lateral to the osteotomy.

Figure 11:
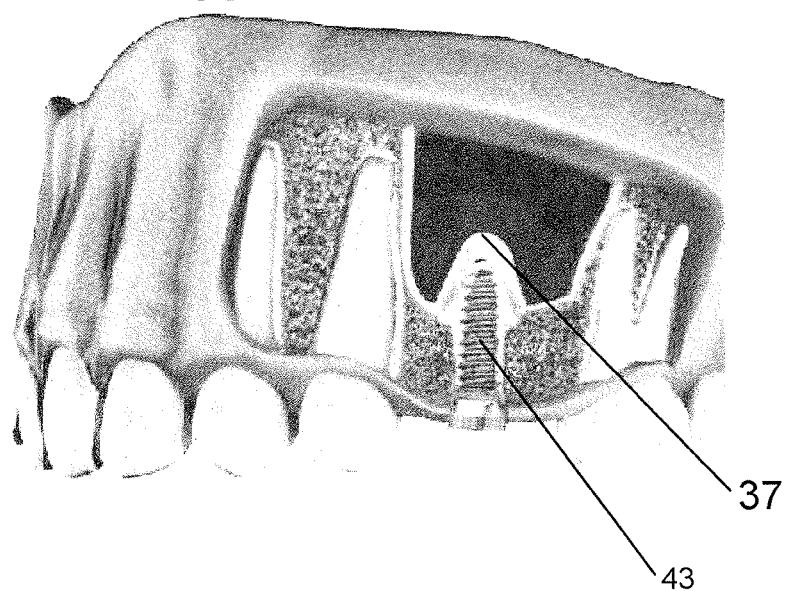

FIG. 11: Perspective view of a previously-edentulous area (cutaway to show sinus cavity) depicting completed placement of implant.

FIG. 12: Perspective view of a first embodiment of sidecutting (lateral relief) drill.

FIG. 13: Perspective view of a second embodiment of sidecutting (lateral relief) drill.

Figure 14:
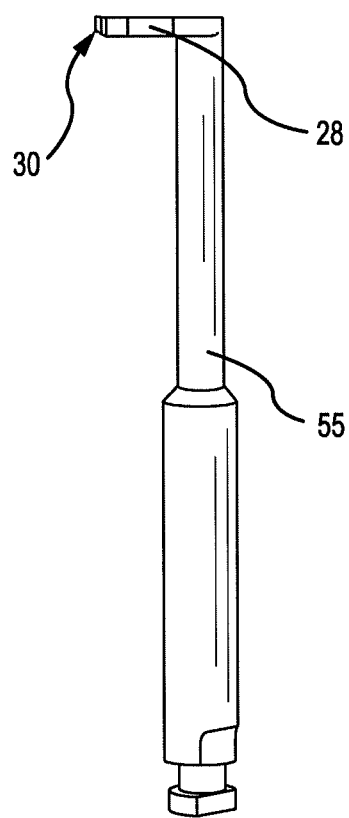

FIG. 14: Side view of first embodiment of sidecutting (lateral relief) drill.

Figure 15:
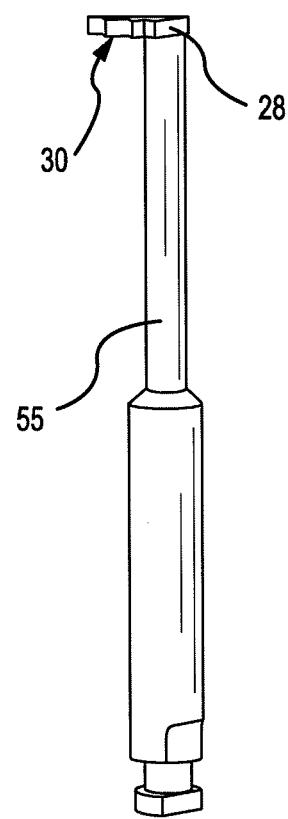

FIG. 15: Side view of second embodiment of sidecutting (lateral relief) drill.

Figure 16:
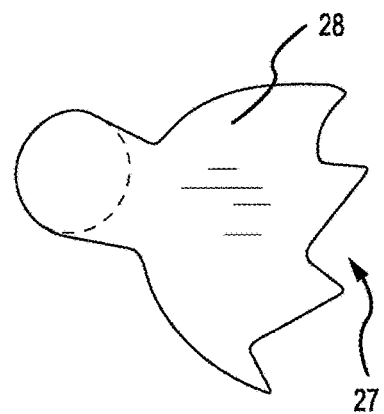

FIG. 16: End view of first embodiment of sidecutting (lateral relief) drill.

Figure 17:
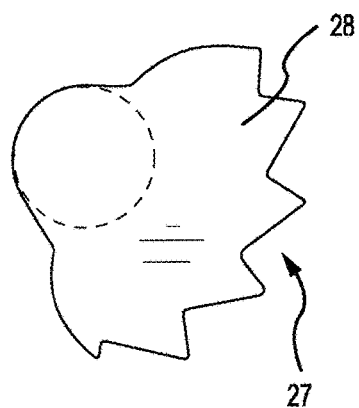

FIG. 17: End view of second embodiment of sidecutting (lateral relief) drill.

Figure 18:
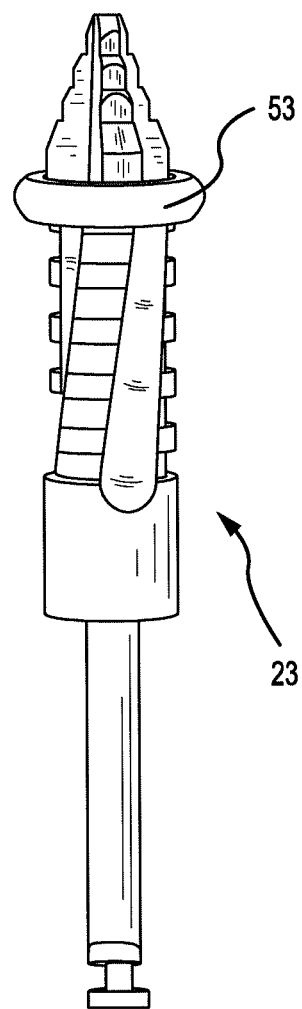

FIG. 18: Side view of a osteotomy former/enlarger drill.

Figure 19:
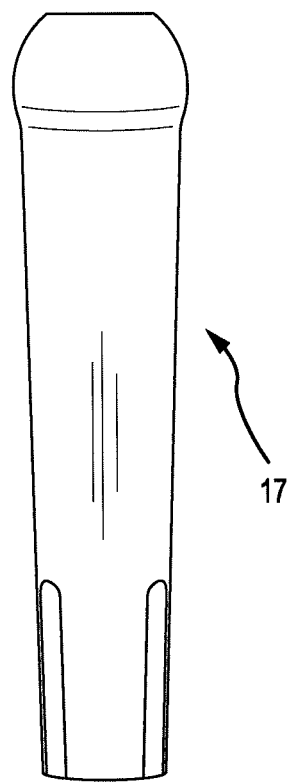

FIG. 19: Side view of a drill stop.

Figure 20:
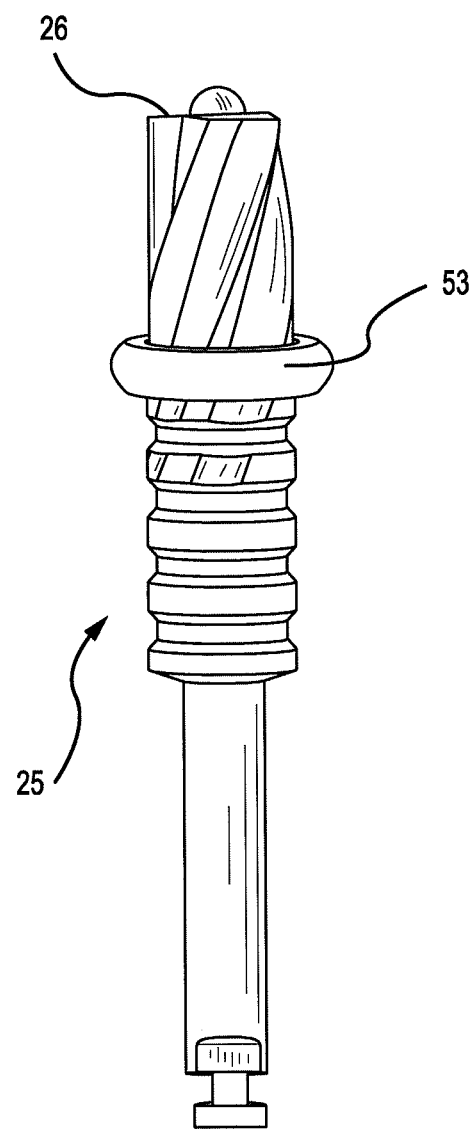

FIG. 20: Side view of a flat tip sinus floor drill.

LIST OF DRAWING REFERENCES

1. Edentulous area
3. Sinus
5. Sinus membrane
7. Bone at Edentulous area
9. Surgical Bur
11. Gingiva
13. Cortical bone
15. Pilot drill
17. Drill stop
19. Tissue punch
21. Center guide pin
23. Osteotomy former/enlarger drill
25. Sinus floor drill (flat tip drill)
26. Flat tip with ½ sphere/ball protrusion
27. Sidecutting drill (lateral relief drill)
28. Nonuniform tip extension
29. Absorbable collagen wound dressing
30. Cutting edge
31. Parallel wall osteotome (concave tip osteotome)
33. Concave tip
35. Osteotomy
37. Lifted sinus floor
39. Bone grafting material
41. Torque wrench
43. Implant
45. Sidecutting drill tip
47. Cutting edge
49. "T"-shaped Osteotomy
51. Bottom of Osteotomy
53. O-ring depth guide
55. Body portion of sidecutting drill
57. Hidden body portion of sidecutting drill just below tip

DESCRIPTION OF THE PREFERRED EMBODIMENTS

With reference to the Figures and all disclosures of this application (including those above and below and those incorporated by reference), the procedure of the present invention comprises using a pilot drill to a depth of between 1 mm and 2 mm from the sinus floor (1 mm to 2 mm below the sinus floor). An osteotomy former/enlarger drill of the desired width and taper is then used to the depth of the pilot hole. A sinus drill is then used to flatten the top of the osteotomy. The sidecutting drill is then used to make relief cuts at the top of the osteotomy (i.e. at the depth where the hole stopped nearest the sinus floor). The result is a "T" shaped osteotomy that will fracture laterally when tapped, thereby allowing the sinus floor to be lifted over an area greater than the area of the bore of the osteotomy (see FIGS. 6 and 9, for example). The sidecutting drill includes a tip extending in a planar nonuniform manner from the centerline of the drill with one or more cutting edges located on the extended portion of the tip for cutting through tissue when the sidecutting drill is rotated (see FIGS. 12 and 13, for example).

The preferred procedure of performing a sinus lift begins by using a surgical bur (#8HS preferred) and high-speed hand piece with water spray to mark the location of the implant placement and drill through the gingival into the cortical bone (FIG. 1). After conducting the necessary accurate measurements with a panoramic or CT x-ray, then the pilot drill is used to a depth of between 1 mm and 2 mm short of (below) the floor of the sinus (FIG. 2). A low speed of 800-1500 rpms is preferred for the pilot speed drill. A drill stop (FIG. 19) is used in conjunction with the pilot drill to stop the drilling at said depth relative to the sinus floor (1-2 mm from sinus floor).

Next, a tissue punch with a center guide pin is used to drill down through the gingiva and to the bone through the periosteum (alternatively, instead of using a tissue punch, a flap can be reflected, allowing direct access to the crestal bone). The tissue punch is guided by the center pin into the pilot hole, removing the gingival tissue plug down to the bone (FIG. 3).

The next step uses an osteotomy former/enlarger drill to open the pilot hole and shape the bore of the hole, allowing entry of the sidecutting drill. The osteotomy former/enlarger preferably includes use of an O-ring as a depth guide (FIGS. 4 and 18).

Then a flat tip sinus floor drill (preferably having a ½ sphere/ball protrusion at the tip) is inserted into the osteotomy (the hole or bore resulting after use of the osteotomy former/enlarger drill) and drills to the depth of the hole established by the pilot drill to shape the end of the hole (bottom of the hole) providing a flat surface to the top of the widened osteotomy (FIGS. 5 and 20).

The next step uses the sidecutting (lateral relief) drill or an ultra sonic bone cutting instrument to make a cut to the side of the hole circumferentially around the bottom of the osteotomy (FIG. 6). Initial rotations of the sidecutting drill may experience some chattering at first but it will then smooth out. The tip of the sidecutting drill (or sidecutting drill bit, as is sometimes fully said or written) is preferably as shown in the figures (FIGS. 12 and 13), but it can also comprise other effective shapes wherein the tip comprises an area of the bit extending horizontally (perpendicularly) from the centerline of the bit, preferably in a nonuniform manner (i.e. it does not extend the same distance in all 360 degrees from the centerline, or necessarily extend at all in some respects of the 360 degrees). When inserted into the osteotomy, the sidecutting bit allows for a circumferential sidecutting or lateral relief cutting action in 360 degrees perpendicular to the long axis (centerline) of the osteotomy. For example, in a first embodiment (FIGS. 12, 14, 16), the portion of the tip extending out from the centerline is a continuous section extending from about 180 degrees of the circumference of the body of the drill bit (see dashed circle indicating hidden body portion just below tip). In a second embodiment (FIGS. 13, 15, 17), the portion of the tip extending out from the centerline is a continuous section extending from about 250 degrees of the circumference of the body of the drill bit. This tip preferably has a cutting surface located on the edge of the side furthest from the centerline of the bit, as depicted in the figures. The tip may also comprise a cutting surface on one or both of the other sides if desired, wherein such side is a leading edge of the tip relative to the direction of rotation of the drill bit. When inserted into the osteotomy, the sidecutting bit allows for a circumferential sidecutting or lateral relief cutting action (FIG. 6). The sidecutting bit is placed at the bottom of the osteotomy and in operation is run circumferentially around the osteotomy. The elongated body of the sidecutting bit itself may also be moved around within the osteotomy in a circumferential manner hugging the outside of the osteotomy, thereby maximizing the cutting performed in creating the top of the "T" shape for the osteotomy. Such action allows the sinus floor to be lifted as described with up-fracturing of the sinus floor over a greater/wider area of the sinus floor than would be possible absent the sidecutting (FIG. 9). The procedure thus also allows a greater amount and depth of bone grafting material to be placed in the osteotomy than would be possible absent the sidecutting step (FIG. 9). But more important is the procedure thus also allows for alveolar bleeding into the lifted graft area reducing the time of resolution of the graft.

The sidecutting drill is in one direction to get maximum lateral cut. For a 4 mm implant, use a 3.5 mm diameter final osteomy drill so the implant will self tap when placed. The distance across the top of the side cutting drill is 3.5 mm so it can be wedged into the osteotomy to the flat top (bottom of the osteotomy, relative to the hole that was drilled) then spun chattering until the shaft is flush to a wall and then rotated around the circular wall to get a "T"-shaped circumferential final shape maximizing the lateral cut. Normally with a straight cut hole and pushing up the membrane, the alveolar bone is sealed off by the implant allowing only the blood supply from the membrane to resolve the graft, changing it to the patient's bone, which takes months. By opening a wedge (when the sinus membrane is upfractured as described herein, a wedge-shaped area is formed due to the circumferential sidecutting) around the implant, and the graft is fed with alveolar bone bleeding, which is rich with osteoclasts and osteoblasts that eat the graft and form new bone plus other bone building elements so resolution is a fraction of the time and the patient's own bone is formed sooner. This results in a situation where an implant can be loaded in a time period between 1 to 2 months, whereas absent the present invention it would normally take 4 to 6 months because of the poor blood supply in the membrane and little leakage from around the implant of alveolar bleeding and healing elements.

After the sidecutting drill is used, the next step is to place a piece of HeliTape® (or alternatively, other absorbable collagen wound dressing for use in dental surgery) into the osteotomy using a concave tip osteotome (size of collagen wound dressing used is preferably about 4 times the size of the osteotomy) (FIG. 7). HeliTAPE® or other similar product protects the wound site (osteotomy), controls bleeding due the hemostatic nature of collagen, and will repair the Schneiderian membrane if perforated. Administration of HeliTape® or other similar product directly in the osteotomy provides a base for the graft material added next.

Next, the osteotomy is filled almost full with a bone grafting material. A concave tip parallel wall osteotome (sometimes simply referred to as an osteotome) sized to match the osteotomy is used to push up (pack) the grafting material and lift the floor of the sinus. The osteotome is thereby used to deliver the Helitape®-type material (preferably used in a membrane form) as well as bone grafting material to the floor of the sinus to be lifted. Grafting material should continue to be added, either pushing on it or tapping with a mallet or other compaction tool, until the desired height of grafting material is achieved.

After completion of the above steps, placement of an implant is the next step. The implant should be firmly seated, until level with the crest of the bone. The implant should now be firmly in place in the jawbone and the grafted bone within the lifted sinus floor. An appropriate implant should be selected based on, among other things, whether a flap was reflected or if it was performed flapless (with a tissue punch, as described above), so as to seal the gingival opening appropriately.

The present invention also encompasses a sinus lift kit comprising instrumentation/tools that can be used in performing the sinus lift procedure. A preferred embodiment of the kit includes the following:
  i. Kit Case
  ii. #8HS Marking Bur
  iii. 1.8 mm Pilot Drill
  iv. 6 mm Drill Stop with O-rings to shorten depth by adding one for each mm shortened
  v. Tissue Punch
  vi. Osteotomy Former/Enlarger
  vii. Sinus Floor Drill
  viii. Sidecutting Drill
  ix. Parallel Wall Osteotome Whereas the figures and descriptions set forth the preferred embodiment of the present invention, it should be apparent to those skilled in the art that various changes may be made in the form of the invention without affecting the scope thereof. The description and figures are not intended in any way to limit the broad features or principles of the invention, or the scope of the patent monopoly to be granted. Likewise, the reference or mention of any brand name product is not intended as a limitation but is instead a mere part of the preferred description, and the scope of the procedure is intended to extend beyond brand names to the generic product(s) itself. References to specific numerical values are only examples of the preferred disclosure without limitation of the scope of the invention or the patent monopoly to be granted.

What is claimed is:

1. A method of performing a sinus lift procedure on a patient at an edentulous site in a jaw bone, the method comprising the steps of:
  a. creating an osteotomy at said edentulous site, said osteotomy having a bottom nearest a floor of said sinus;
  b. performing a lateral relief cut at said bottom of said osteotomy, wherein said step of performing a lateral relief cut comprises making a circumferential cut such that the area of the lateral relief cut is wider than the rest of the osteotomy;
  c. pushing bone grafting material into said osteotomy;
  d. lifting said floor of said sinus by said step of pushing.

2. The method of claim 1 wherein said circumferential cut is performed in a direction perpendicular to the long axis centerline of said osteotomy.

3. The method of claim 2 wherein performing said circumferential cut forms a "T"-shaped osteotomy, wherein said lateral relief cut forms the top of the "T".

4. A method of performing a sinus lift procedure on a patient at an edentulous site in a jaw bone, the method comprising the steps of:
  a. creating an osteotomy at said edentulous site, said osteotomy having a bottom nearest a floor of said sinus;

b. performing a lateral relief cut at said bottom of said osteotomy;
c. pushing bone grafting material into said osteotomy;
d. lifting said floor of said sinus by said step of pushing, wherein said step of lifting said sinus floor comprises upfracturing of said sinus floor over an area greater than the cross-sectional area of said osteotomy.

5. A method of performing a sinus lift procedure on a patient at an edentulous site in a jaw bone, the method comprising the steps of:
   a. creating an osteotomy at said edentulous site, said osteotomy having a bottom nearest a floor of said sinus;
   b. performing a lateral relief cut at said bottom of said osteotomy, wherein said step of performing a lateral relief cut forms a "T"-shaped osteotomy, wherein said lateral relief cut forms the top of the "T";
   c. pushing bone grafting material into said osteotomy;
   d. lifting said floor of said sinus by said step of pushing.

* * * * *